US010986868B2

(12) United States Patent
Chen (10) Patent No.: US 10,986,868 B2
(45) Date of Patent: Apr. 27, 2021

(54) ELECTRONIC ATOMIZING DEVICE WITH A LIQUID GUIDING EFFECT AND ATOMIZER

(71) Applicant: Shenzhen Smoore Technology Limited, Shenzhen (CN)

(72) Inventor: Zhiping Chen, Shenzhen (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 369 days.

(21) Appl. No.: 16/065,356

(22) PCT Filed: Feb. 19, 2016

(86) PCT No.: PCT/CN2016/074096
§ 371 (c)(1),
(2) Date: Jun. 22, 2018

(87) PCT Pub. No.: WO2017/139963
PCT Pub. Date: Aug. 24, 2017

(65) Prior Publication Data
US 2020/0120983 A1    Apr. 23, 2020

(51) Int. Cl.
*A24F 13/00* (2006.01)
*A24F 17/00* (2006.01)
*A24F 25/00* (2006.01)
*A24F 40/48* (2020.01)
*A24F 40/70* (2020.01)
*A24F 40/10* (2020.01)
*A24F 40/46* (2020.01)
(Continued)

(52) U.S. Cl.
CPC .............. *A24F 40/48* (2020.01); *A24F 40/10* (2020.01); *A24F 40/44* (2020.01); *A24F 40/46* (2020.01); *A24F 40/70* (2020.01); *H05B 3/34* (2013.01); *H05B 2203/013* (2013.01); *H05B 2203/021* (2013.01)

(58) Field of Classification Search
CPC ...... A24F 47/008; A24F 47/002; A24F 40/10; A24F 40/40; A24F 40/44; A24F 40/46; A24F 40/48
USPC .................................................. 131/329, 328
See application file for complete search history.

(56) References Cited

U.S. PATENT DOCUMENTS

| 9,504,279 B2 | 11/2016 | Chen |
| 9,603,389 B2 | 3/2017 | Chen |
| 2015/0090280 A1 | 4/2015 | Chen |

(Continued)

FOREIGN PATENT DOCUMENTS

| AU | 2014206215 A1 | 8/2014 |
| CN | 102326869 A | 1/2012 |

(Continued)

*Primary Examiner* — Hae Moon Hyeon
(74) *Attorney, Agent, or Firm* — Coats & Bennett, PLLC (57) ABSTRACT

An electronic atomizing device, comprising a body and an atomizing element; the body is provided with an e-liquid storage cavity and an air suction channel; the atomizing element comprises a porous body and a heating structure; the porous body comprises an e-liquid suction surface, an atomizing surface and a side surface; the e-liquid suction surface is used for drawing e-liquid from the liquid storage cavity, and the heating structure is located on the atomizing face; at least one section of the airflow channel extends to the interior of the porous body from the side surface.

19 Claims, 8 Drawing Sheets

(51) Int. Cl.
*A24F 40/44* (2020.01)
*H05B 3/34* (2006.01)

(56) References Cited

U.S. PATENT DOCUMENTS

| | | | | |
|---|---|---|---|---|
| 2016/0073694 A1* | 3/2016 | Liu | ................. | H05B 3/40 |
| | | | | 131/329 |
| 2016/0106153 A1* | 4/2016 | Zhu | ................. | H05B 3/44 |
| | | | | 131/329 |
| 2016/0135505 A1* | 5/2016 | Li | ................. | A24F 47/008 |
| | | | | 131/329 |
| 2016/0143365 A1* | 5/2016 | Liu | ............... | A61M 15/06 |
| | | | | 131/329 |
| 2016/0192710 A1* | 7/2016 | Liu | .............. | H05B 3/0014 |
| | | | | 131/329 |
| 2017/0112193 A1* | 4/2017 | Chen | ............ | A24F 47/008 |
| 2019/0223504 A1* | 7/2019 | Chen | ............ | A24F 47/008 |

FOREIGN PATENT DOCUMENTS

| | | |
|---|---|---|
| CN | 202276831 U | 6/2012 |
| CN | 103932401 A | 7/2014 |
| CN | 104055223 A | 9/2014 |
| CN | 204317492 U | 5/2015 |
| CN | 104872822 A | 9/2015 |
| CN | 104983079 A | 10/2015 |
| CN | 105559147 A | 5/2016 |
| CN | 205695694 U | 11/2016 |
| EP | 2946678 A1 | 11/2015 |
| EP | 3020292 A1 | 5/2016 |

* cited by examiner

ELECTRONIC ATOMIZING DEVICE WITH A LIQUID GUIDING EFFECT AND ATOMIZER

TECHNICAL FIELD

The present disclosure relates to smoking articles technical field, and more particularly relates to an electronic atomizing device.

BACKGROUND

Electronic cigarettes are also known as virtual cigarettes. An atomizing element of the electronic cigarette may use a porous body, which however often has a problem that an effect of guiding liquid is not good.

SUMMARY

Accordingly, it is necessary to provide an electronic cigarette with a good liquid guiding effect, and an atomizer thereof.

An electronic atomizing device includes a body and an atomizing element. The body defines a liquid storage chamber and an inhalation channel. The atomizing element includes a porous body and a heat generating structure. The porous body includes a liquid absorbing surface, an atomizing surface and a side surface. The liquid absorbing surface is used for absorbing liquid from the liquid storage chamber. The heat generating structure is located on the atomizing surface. The porous body forms an airflow channel thereon. The airflow channel flows through the atomizing surface and is in communication with the inhalation channel. At least one segment of the airflow channel extends from the side surface towards an interior of the porous body.

In the above-mentioned electronic atomizing device, the liquid absorbing surface is used for absorbing liquid in the liquid storage chamber. The heat generating structure on the atomizing surface is used for atomizing the liquid. Smoke generated at the atomizing surface enters the airflow channel with an airflow. At least one segment of the airflow channel extends from the side surface towards the interior of the porous body. The segment of the airflow channel on the one hand can reduce a cross-sectional area of a heat conducting path from the atomizing surface to the liquid absorbing surface, and on the other hand can take away a large amount of heat conducted from the atomizing surface towards the liquid absorbing surface, which can greatly reduce the heat conducted from the atomizing surface towards the liquid absorbing surface, and avoid an internal overheat of the porous body, resulting in an expansion of the liquid or gas in the porous body which cause a high fluid pressure in the porous body to impede a transmission of the liquid, therefore improving a liquid guiding effect of the porous body, at the same time, avoid that the liquid in the liquid storage chamber absorbs a lot of heat from the liquid absorbing surface, which results in waste of energy, and further avoid that a temperature of the liquid increases so much that a composition of the liquid composition changes. At the same time, as the airflow can generate a negative pressure, the negative pressure can further accelerate the transport of the liquid.

BRIEF DESCRIPTION OF THE DRAWINGS

In order to describe the technical solutions in the embodiments of the present application or in the prior art more clearly, the following briefly introduces the accompanying drawings required for describing the embodiments or the prior art. Apparently, the accompanying drawings in the following description merely show some embodiments of the present application. For those of ordinary skill in the art, other drawings can be acquired based on these drawings without any creative work.

DETAILED DESCRIPTION OF THE EMBODIMENTS

In order to facilitate understanding of the present disclosure, a more comprehensive description of an electronic atomizing device will be provided below with reference to the accompanying drawings. A preferred embodiment of the electronic atomizing device is given in the drawings. However, the electronic atomizing device can be implemented in many different forms and is not limited to the embodiments described in this disclosure. Rather, these embodiments are provided so that this disclosure of the electronic atomizing device will be thorough and complete.

Unless the context clearly requires otherwise, all technical and scientific terms used herein have the same meaning as commonly understood by one of ordinary skill in the art to which this invention belongs. The terms used in the description of the electronic atomizing device in the present disclosure is merely for the purpose of describing specific embodiments and is not intended to limit the present disclosure. As used herein, the term "and/or" includes any and all combinations of one or more of the associated items in the list.

Figure 1:
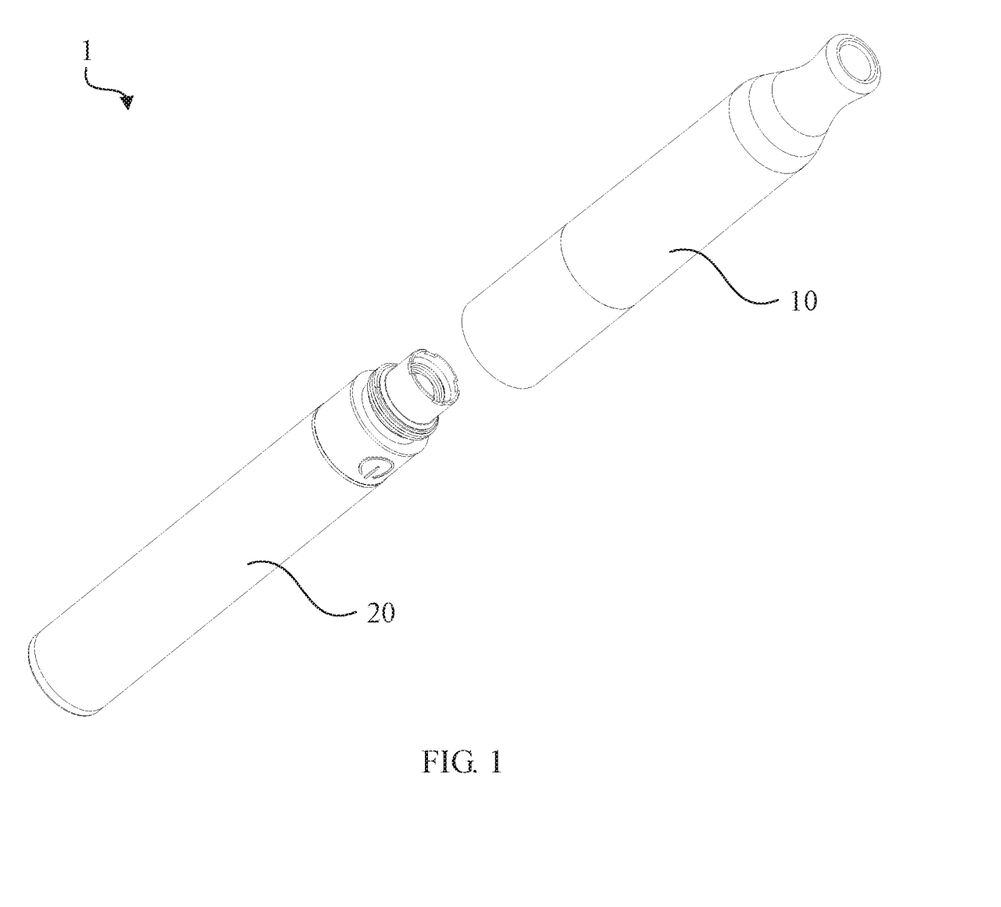
FIG. 1 is a perspective view of an electronic cigarette in accordance with an embodiment.

As shown in FIG. 1, an electronic cigarette 1 according to an embodiment includes an atomizer 10 and a battery device 20. The atomizer 10 and the battery device 20 can be detachably connected, such as a screw connection. The battery device 20 is used for providing power supply for the atomizer 10. An electronic atomizing device according to one embodiment can be the electronic cigarette 1, or can be only the atomizer 10 of the electronic cigarette 1.

Figure 2:
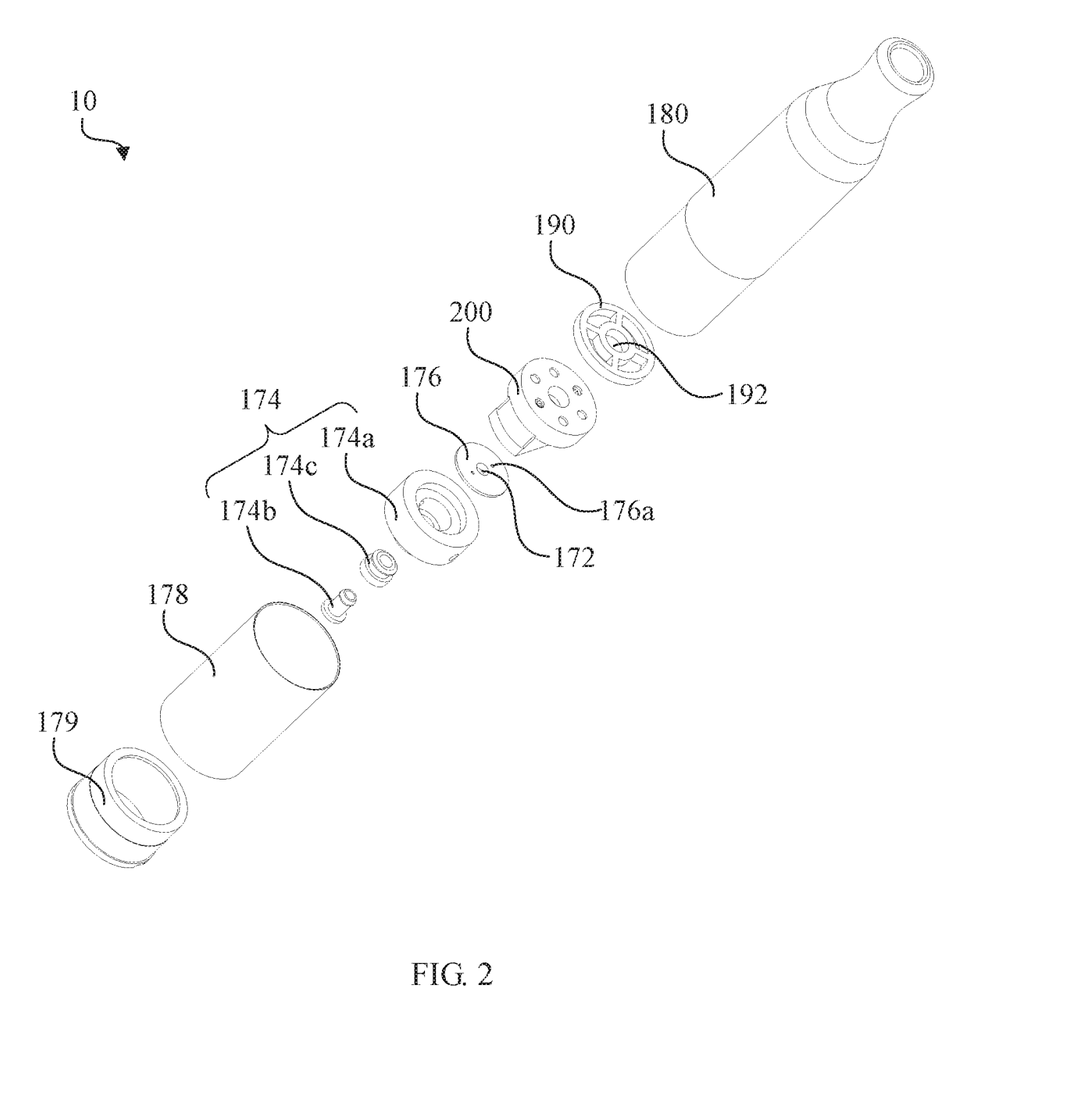
FIG. 2 is an exploded view of an atomizer of the electronic cigarette shown in FIG. 1.
Figure 3:
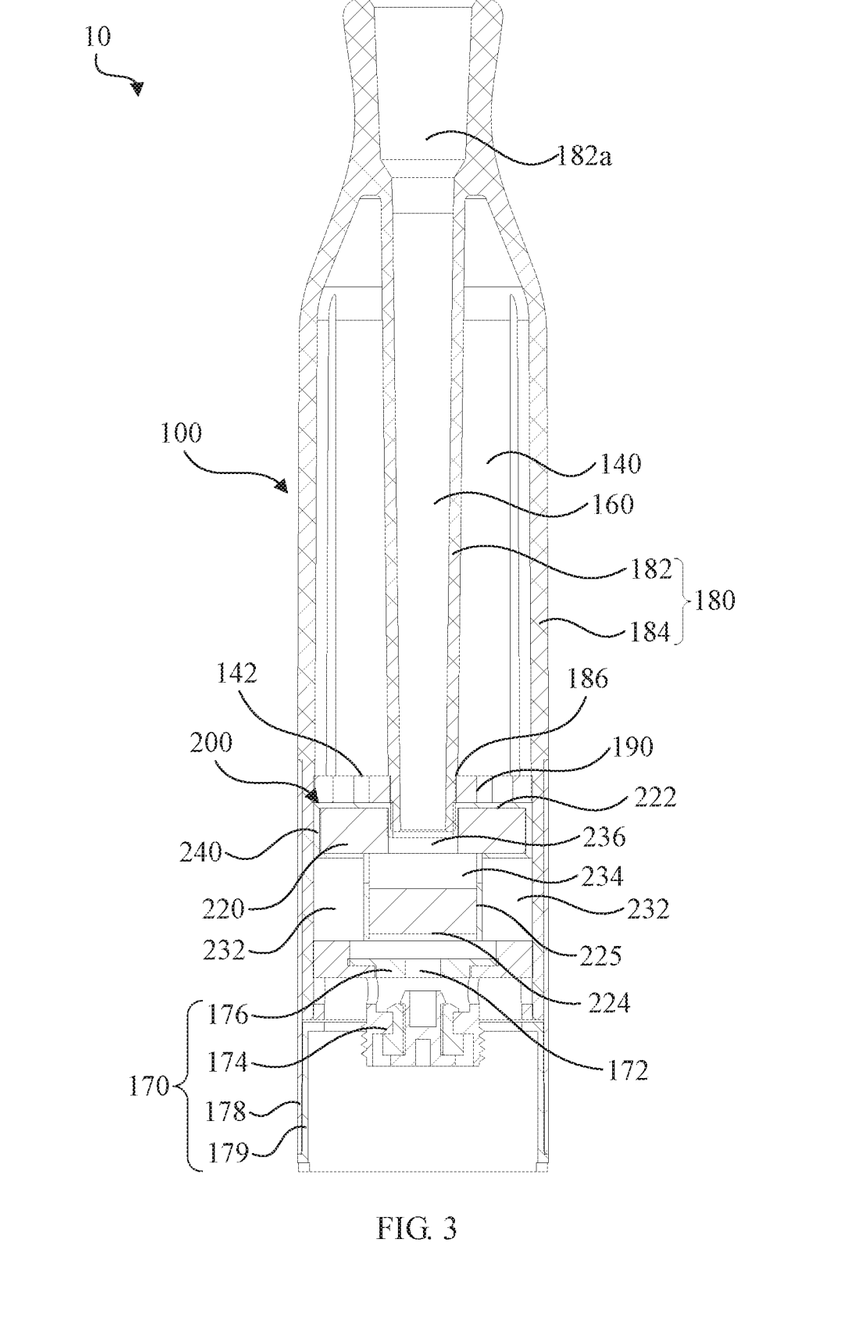
FIG. 3 is a cross-sectional view of the atomizer in the electronic cigarette shown in FIG. 1.

Referring to FIGS. 2 and 3, the atomizer 10 includes a body 100 and an atomizing element 200. The body 100 is provided with a liquid storage chamber 140 and an inhalation channel 160 therein. The atomizing element 200 includes a porous body 220 and a heat generating structure (not shown in the drawings). The porous body 220 includes a liquid absorbing surface 222, an atomizing surface 224, and a side surface 225. The liquid absorbing surface 222 is used for absorbing liquid from the liquid storage chamber 140. The heat generating structure is located on the atomizing surface 224. The battery device 20 is used for supplying power to the heat generating structure.

An airflow channel is formed on the porous body 220. The airflow channel flows through the atomizing surface 224 and is in communication with the inhalation channel 160. At least one segment of the airflow channel extends from the side surface 225 toward an interior of the porous body 220. Specifically, in an embodiment, the airflow channel can include a plurality of sub-channels that are angled to each other. The sub-channels are respectively located inside the porous body 220, and between the porous body 220 and the body 100. At least one sub-channel extends from the side surface towards the interior of the porous body 220.

The liquid absorbing surface 222 is used for absorbing the liquid in the liquid storage chamber 140. The heat generating structure on the atomizing surface 224 is used for atomizing the liquid. The smoke generated at the atomizing surface 224 enters the airflow channel along with an airflow. At least one segment of airflow channel extends from the side surface towards the interior of the porous body 220. The segment of the airflow channel, on one hand, can reduce a cross-sectional area of a heat conducting path from the atomizing surface to the liquid absorbing surface. On the other hand, it can take away a large amount of heat conducted from the atomizing surface to the liquid absorbing surface, so that the heat conducted from the atomizing surface towards the liquid absorbing surface can be greatly reduced. Therefore, it can be avoided that an internal overheat of the porous body results in an expansion of the liquid or gas in the porous body. Thus, a high fluid pressure in the porous body which impedes a transmission of the liquid can be avoided, therefore improving a liquid guiding effect of the porous body. At the same time, it can be avoided that the liquid smoke in the liquid storage chamber absorbs a lot of heat from the liquid absorbing surface, which results in waste of energy, and it can be further avoided that a temperature of the liquid increases so much that a composition of the liquid composition changes. At the same time, the airflow can generate a negative pressure, which can further accelerate the transport of the liquid.

The heat generating structure can be a heating circuit layer or a heating film. The heating circuit layer can be plated on the atomizing surface 224. The heating film can be a porous heating film. The porous heating film is formed on the atomizing surface 224 by a vapor deposition method. A thickness of the porous heating film is in a range from 0.5 μm to 1.5 μm. Micropores on the porous heating film can greatly increase a contact area with the liquid and improve an atomizing efficiency. Preferably, the thickness of the porous heating film is 0.8 μm to 1 μm.

The porous heating film is located on the atomizing surface 224 of the porous body 220, so that an atomized liquid can be easily discharged from the porous body 220. The porous heating film can uniformly heat a surface of the porous body 220, so that the atomizing temperature is uniform. Accordingly, a problem of large atomized particles caused by low local temperatures will not occur, ensuring that the atomized particles are uniform, and a taste of the electronic cigarette 1 is improved. In an embodiment, an aperture of the micropore on the porous heating film is in a range from 5 μm to 30 μm. Preferably, the thickness of the porous heating film is less than the aperture of the micropore on the porous body 220.

In an embodiment, the porous body 220 is a porous ceramic body, the aperture of the micropore on the porous body 220 is in a range from 1 μm to 100 μm, and a porosity of the porous body 220 is in a range from 30% to 83%. A size of the porosity can be adjusted according to a different composition of the liquid. For example, the larger of a viscosity of the liquid, and the higher of the porosity. Preferably, in one embodiment, a volume of the micropores with the aperture of 5 μm to 30 μm on the porous body 220 accounts for more than 60% of a volume of all the micropores on the porous body 220, and the porous body 220 has a moderate infiltration effect.

Figure 4:
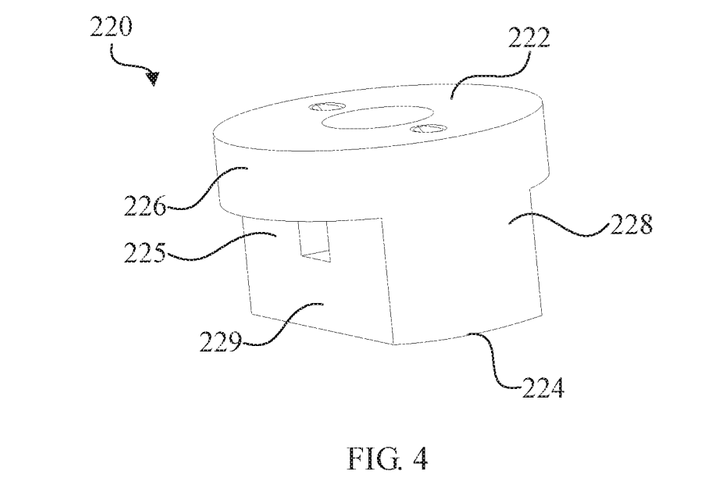
FIG. 4 is a perspective view of a porous body in the electronic cigarette shown in FIG. 1.

Referring also to FIG. 4, in one embodiment, the porous body 220 includes a liquid absorbing portion 226, an atomizing portion 228, and a liquid guiding portion 229 disposed between the liquid absorbing portion 226 and the atomizing portion 228, which are integrally formed. The liquid absorbing surface 222 is located on a side of the liquid absorbing portion 226 away from the liquid guiding portion 229, and the atomizing surface 224 is located on a side of the atomizing portion 228 away from the liquid guide portion 229.

The sub-channel includes a first sub-channel 232, a second sub-channel 234 and a third sub-channel 236 that are sequentially communicated. The first sub-channel 232 is formed by enclosing a sidewall of the atomizing portion 228, a sidewall of the liquid guiding portion 229 and an inner wall of the body 100. The second sub-channel 234 is located inside the liquid guiding portion 229. The second sub-channel 234 extends from a side surface 225 towards an interior of the liquid guiding portion 229. The third sub-channel 236 is located inside the liquid absorbing portion 226, and the third sub-channel 236 is in communication with the inhalation channel 160. The atomizing surface 224 generates atomizing effect. Airflow goes with the smoke at the atomizing surface 224, enters the first sub-channel 232, then enters the third sub-channel 236 through the second sub-channel 234, and finally enters the mouth of a user through the inhalation channel 160.

Specifically, in one embodiment, the number of the first sub-channel 232 and the number of the second sub-channel 234 are both two. The number of the third sub-channel 236 is one, and the third sub-channel 236 is located in a middle portion of the liquid absorbing portion 226. One end of each of the two second sub-channels 234 is in communication with each of the two first sub-channels 232, and the other ends of each of the two second sub channels 234 is in communication with the third sub channel 236. In other embodiments, the number of the first sub-channel 232 and the number of the second sub-channel 234 can also be three or four. If the number of the first sub-channel 232 and the number of the second sub-channel 234 is less, a machining thereof is more convenient, and if the number of the first sub-channel 232 and the number of the second sub-channel 234 is more, a heat dissipation thereof is better.

Referring again to FIG. 3, in an embodiment, the body 100 includes a liquid reservoir 180 that includes an inner tube 182 and an outer tube 184. The inhalation channel 160 is located inside the inner tube 182. One end of the inner tube 182 extends into the third sub-channel 236, so that the inhalation channel 160 is in communication with the third sub-channel 236. The liquid absorbing portion 226 can have an annular shape. The third sub-channel 236 allows air to flow and at the same time is used for mounting and fixing. The other end of the inner tube 182 forms an absorbing port 182a. The user inhales smoke through the absorbing port 182a. The inner tube 182 is received in the outer tube 184. The liquid storage chamber 140 is located between the outer tube 184 and the inner tube 182, and has an opening 142 facing the atomizing element 200. The atomizing element 200 is located in the outer tube 184 and is adjacent to the liquid storage chamber 140. The liquid absorbing surface 222 faces the liquid storage chamber 140, and covers the opening 142 of the liquid storage chamber 140. The inner tube 182 may be located at the center of the outer tube 184 or may be offset from the center of the outer tube 184. A position of the third sub-channel 236 can correspond to a position of the inner tube 182.

Referring to FIGS. 2 and 3, in an embodiment, the body 100 further includes a flow restricting member 190. As a non-essential element, The flow restricting member 190 is used to limit an amount of the liquid conducted to the liquid absorbing surface 222, and can be omitted. In one embodiment, the flow restricting member 190 can be a plastic member defining holes for conducting liquid. In other embodiments, the flow restricting member 190 can be made of a porous material, therefore there is no need to have holes for conducting liquid. In one embodiment, the liquid absorbing surface 222 is provided with a groove (not shown in the figure). The groove can increase a contact area with the liquid and increase a liquid guiding speed.

In this embodiment, the flow restricting member 190 defines a mounting hole 192 matching the inner tube 182. The flow restricting member 190 is sleeved on the inner tube 182 via the mounting hole 192. The flow restricting member 190 is located at a junction position between the liquid storage chamber 140 and the liquid absorbing surface 222. An outer wall of the inner tube 182 and/or an inner wall of the outer tube 184 are provided with a step portion 186, and the flow restricting member 190 is latched on the step portion 186 to facilitate an installation thereof.

Figure 5:
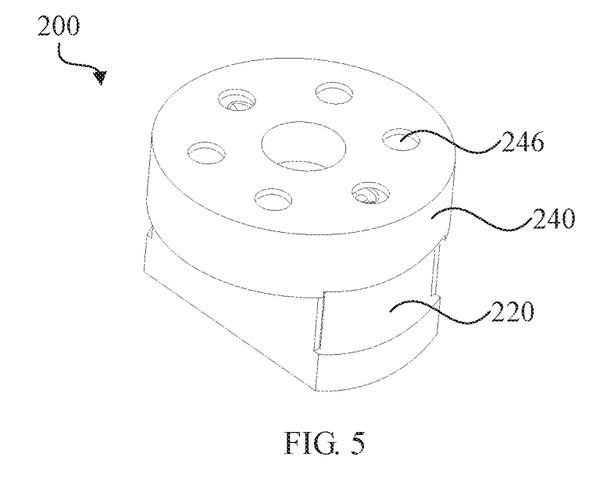
FIG. 5 is a perspective view of an atomizing element in the electronic cigarette shown in FIG. 1.
Figure 6:
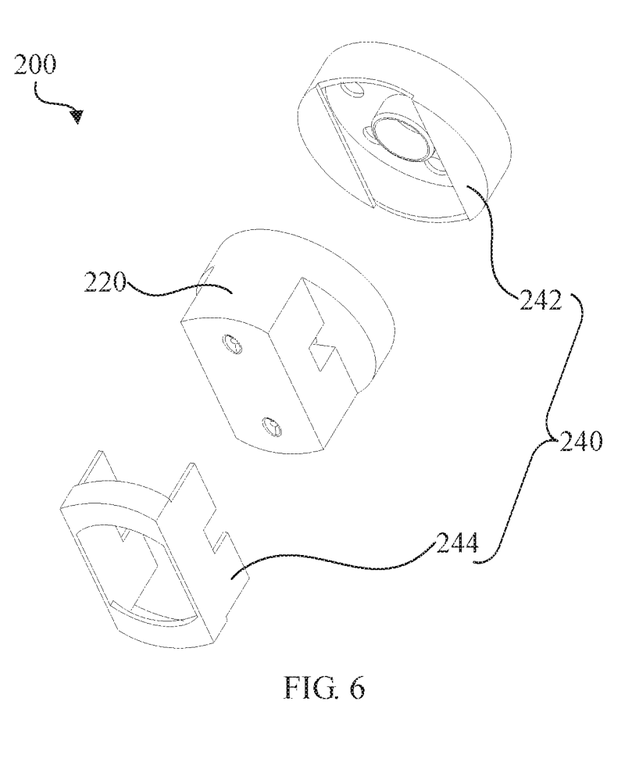
FIG. 6 is an exploded view of the atomizing element in the electronic cigarette shown in FIG. 1.

Referring to FIGS. 5 and 6 simultaneously, the atomizing element 200 further includes a sealing gasket 240. The sealing gasket 240 enwraps the porous body 220. The sealing gasket 240 can include a first portion 242 and a second portion 244 to facilitate machining and assembly. The sealing gasket 240 can be made of silicone material, or can be made of other materials having sealing and heat insulation functions. The sealing gasket 240 enwraps the porous body 220 to reduce an unnecessary volatilization of the liquid, and at the same time, has a heat insulation effect to prevent an outer housing of the electronic cigarette 1 from being overheated and save energy. The silicone gasket can also avoid hard contact between the porous body 220 and other components, thus avoiding a damage of the porous body 220.

Specifically, in an embodiment, the sealing gasket 240 can cover the liquid absorbing surface 222 and a junction portion between the liquid absorbing portion 226 and the inner tube 182 to seal a gap between the porous body 220 and the inner tube 182. The sealing gasket 240 covering the liquid absorbing surface 222 is provided with a flow restricting hole 246, so as to limit the flow. In an embodiment, the sealing gasket 240 can further cover the sidewall of the atomizing portion 228 and the sidewall of the liquid guiding portion 229 which are used for forming the first sub-channel 232, so as to avoid the volatilization of liquid at the sidewalls. At the same time, due to the atomizing of the atomizing portion 228, an internal pressure thereof is small and an airflow is easy to enter. The sealing gasket 240 at the sidewall can prevent the airflow from entering the porous body 220 and affecting a liquid guiding, thus further improving the liquid guiding effect.

Figure 7:
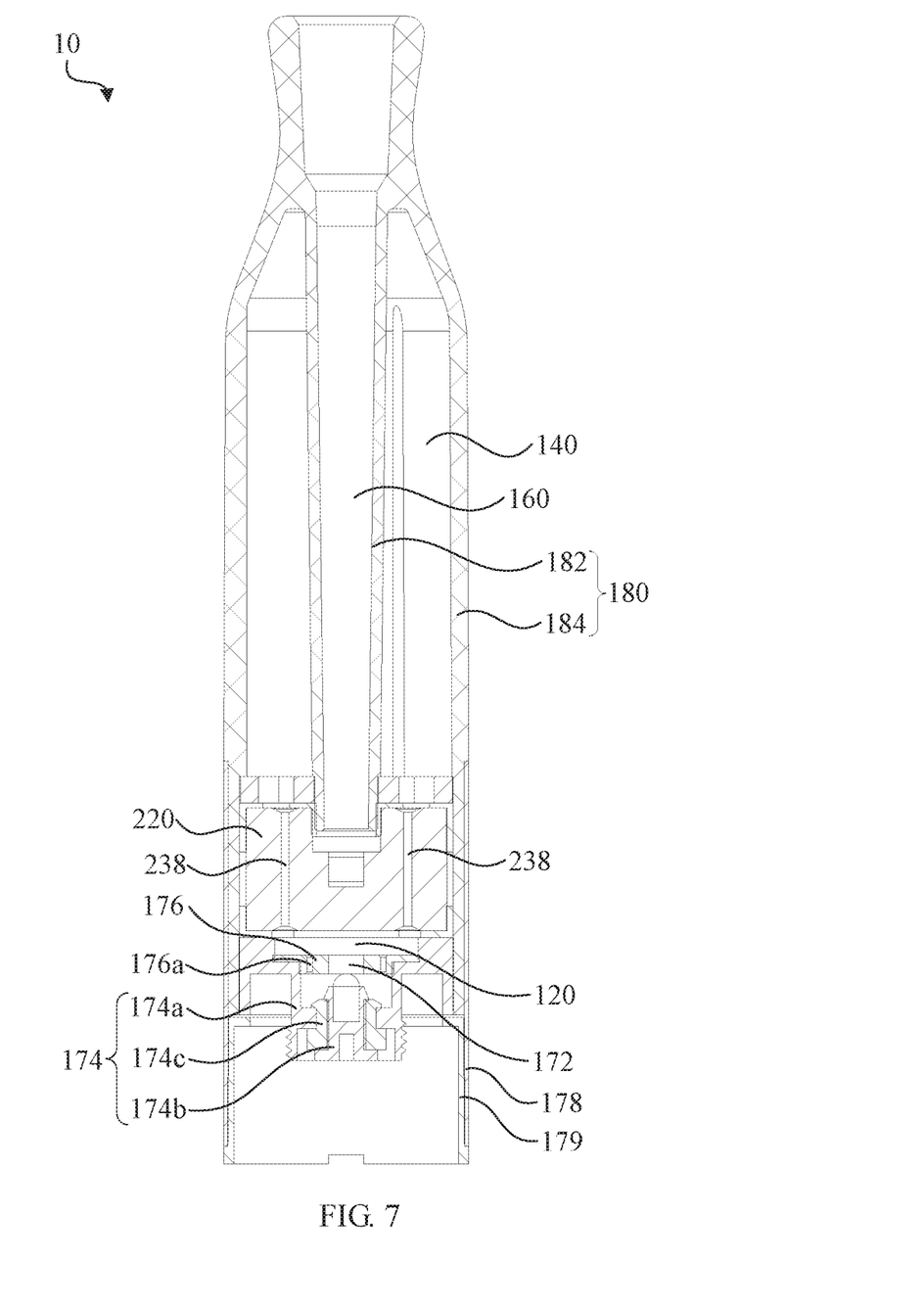
FIG. 7 is a cross-sectional view of the atomizer in the electronic cigarette shown in FIG. 1 viewed from another aspect.

Referring to FIG. 7 simultaneously, a wire is used for supplying power to the heat generating structure, one end of the wire extends from the atomizing surface 224 through the porous body 220 and is welded and fixed on the liquid absorbing surface 222 to ensure that the wire is firmly connected. The wire of the heat generating structure is not shown in FIG. 7, and a wire hole 238 reserved for the wire in the porous body 220 can be seen in FIG. 7.

Referring to FIGS. 2, 3, and 7 simultaneously, in one embodiment, the body 100 further includes a connecting structure 170. The atomizing element 200 is fixed within the body 100 by the connecting structure 170. The connecting structure 170 defines an air inlet 172 aligned with the atomizing surface 224, so as to facilitate a removal of the smoke generated by the atomizing. Preferably, in one embodiment, an axial direction of the air inlet 172 is perpendicular to the atomizing surface 224.

In an embodiment, the connecting structure 170 can include an electrical connecting assembly 174 and a wire positioning member 176. The wire positioning member 176 is disposed on the electrical connecting assembly 174. The wire positioning member 176 is provided with a wire hole 176a for limiting a position of the wire of the heat generating structure, so as to avoid a short caused by a wrong contact between the wire and the electrical connecting assembly 174. In one embodiment, the electrical connecting assembly 174 can include a negative electrode connector base 174a, a positive electrode connector 174b, and an insulating sleeve 174c disposed between the negative electrode connector base 174a and the positive electrode connector 174b. A positive electrode wire of the heat generating structure is connected to the positive electrode connector 174b through the wire hole 176a. A negative electrode wire of the heat generating structure is connected to the negative electrode connector 174a through another wire hole 176a. In one embodiment, the positive electrode connector 174b is located at the center of the negative electrode connector base 174a. The negative electrode connector base 174a can be provided with a vent hole. The air inlet 172 can be defined on the wire positioning member 176.

Further, in an embodiment, the atomizing element 200 is fixed within the outer tube 184 by the connecting structure 170. The connecting structure 170 can further include a confining tube 178 and a blocking member 179. The confining tube 178 is sleeved on the outer wall of the outer tube 184. The electrical connecting assembly 174 abuts against the inner wall of the outer tube 184, and a position of the confining tube 178 corresponds to a position of the electrical connecting assembly 174 correspond. The liquid reservoir 180 can be made of plastic material. The confining tube 178 can be a steel tube to clamp the liquid reservoir 180 with the outer tube 184 from opposite sides, which makes a connection thereof more secure. The blocking member 179 extends into the confining tube 178. An end of the blocking member 179 abuts against the outer tube 184 and the electrical connecting assembly 174. The blocking member 179 can be made of metal material, and the blocking member 179 can be integrated with a screw sleeve of the electrical connecting assembly 174. For ease of machining, the blocking member 179 can also be riveted with the confining tube 178, so that a connection thereof is more secure, preventing the electrical connecting assembly 174 from falling off. If the blocking member 179 is directly riveted with a plastic outer tube 184, a binding force thereof is relatively weak.

In the atomizer 10 of the above embodiment, an entire structure is assembled very conveniently due to a clever cooperation among the components. During assembly, in the first step, the liquid is injected into the liquid reservoir 180 having the confining tube 178 attached thereto. In the second step, the atomizing element 200 is fixed to and electrically connected to the electrical connecting assembly 174. In the third step, the atomizing element 200 is mounted into the liquid reservoir 180 together with the electrical connecting assembly 174. At this time, the atomizing element 200 can be directly sleeved on the inner tube 182. If the flow restricting member 190 is provided, it can be firstly sleeved on the inner tube 182. In the fourth step, the blocking member 179 is riveted into the confining tube 178 and abuts against the electrical connecting assembly 174 to complete the assembly.

Figure 8:
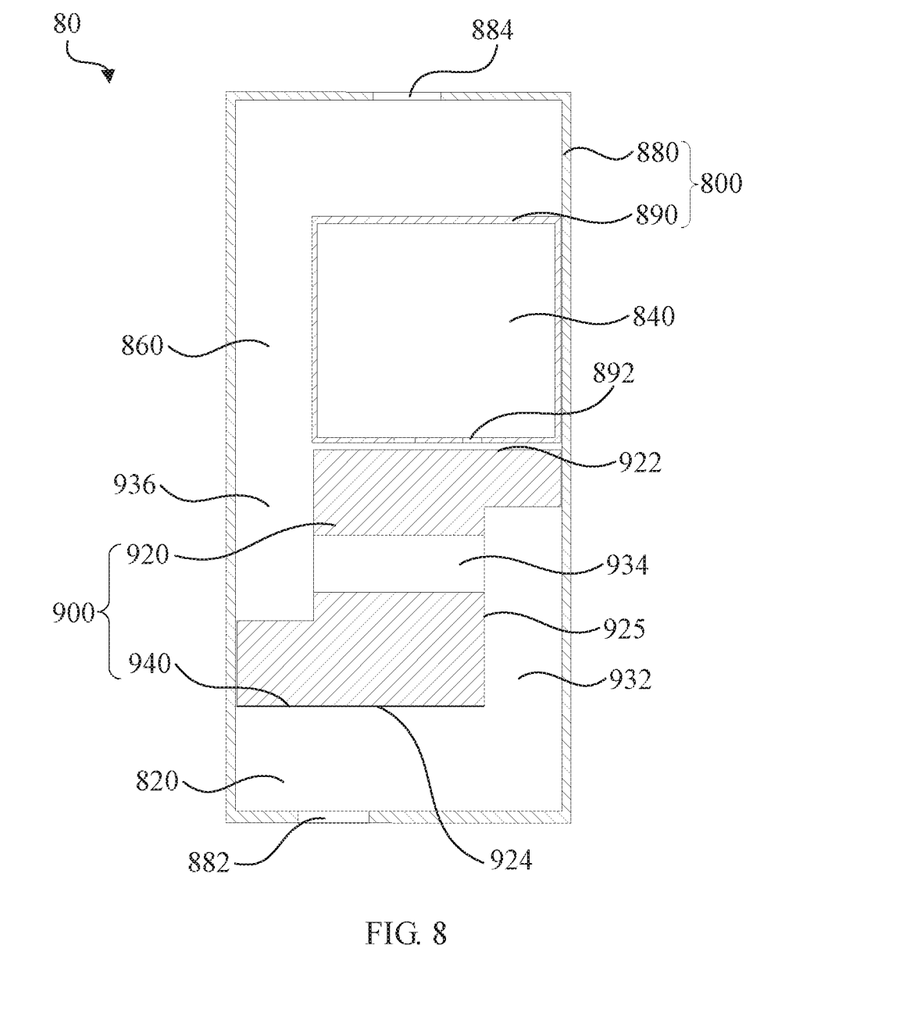
FIG. 8 is a cross-sectional view of an electronic cigarette in accordance with another embodiment.
Figure 9:
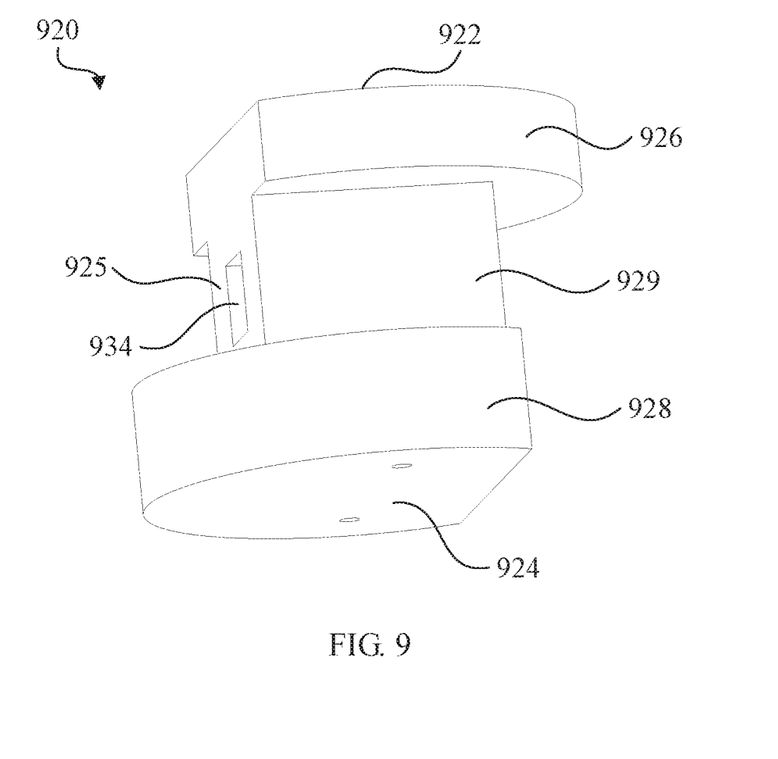
FIG. 9 is a perspective view of a porous body in the electronic cigarette shown in FIG. 8.

Referring to FIGS. 8 and 9, in another embodiment, the atomizer 80 of the electronic cigarette includes a body 800 and an atomizing element 900. The body 800 is provided with an atomizing chamber 820, a liquid storage chamber 840, and a inhalation channel 860.

Specifically, in an embodiment, the body 800 includes a housing 880 and a liquid reservoir 890. The liquid reservoir 890 and the atomizing element 900 are located within the housing 880. The atomizing chamber 820 is located between an inner wall of the housing 880 and the atomizing element 900. The liquid storage chamber 840 is located within the liquid reservoir 890. The inhalation channel 860 is located between the inner wall of the housing 880 and the liquid reservoir 890. The housing 880 defines an air inlet 882 and an air outlet 884. The air inlet 882 is in communication with the atomizing chamber 820. The air outlet 884 is in communication with the inhalation channel 860.

The atomizing element 900 includes a porous body 920 and a heat generating structure 940. The material and the microstructure of the porous body 920 and the heat generating structure 940 can be the same as those of the embodiments shown in FIGS. 1 to 7. The porous body 920 includes a liquid absorbing surface 922, an atomizing surface 924, and a side surface 925. The liquid absorbing surface 922 is used for absorbing liquid from the liquid storage chamber 840. In one embodiment, the liquid reservoir 890 is provided with a liquid outlet hole 892. The liquid in the liquid storage chamber 840 flows out from the liquid outlet hole 892 and flows onto the liquid absorbing surface 922. The heat generating structure 940 is located on the atomizing surface 924. An airflow channel is formed on the porous body 920. The airflow channel is communicated between the atomizing chamber 820 and the inhalation channel 860. At least one segment of the airflow channel extends from the side surface 925 towards an interior of the porous body 920.

The porous body 920 is an integrally formed structure. The porous body 920 includes a liquid absorbing portion 926, an atomizing portion 928, and a liquid guiding portion 929 located between the liquid absorbing portion 926 and the atomizing portion 928. The liquid absorbing surface 922 is located on a side of the liquid absorbing portion 926 away from the liquid guide portion 929, and the atomizing surface 924 is located on a side of the atomizing portion 928 away from the liquid guiding portion 929.

In an embodiment, the airflow channel can include a plurality of sub-channels that are angled with each other. The a plurality of sub-channels are respectively located inside the porous body 920 and between the porous body 920 and the body 800. The airflow channel includes a plurality of sub-channels that are angled with each other. The sub-channels are formed inside the porous body 920 or between the porous body 920 and the body 800. The sub-channels include a first sub-channel 932, a second sub-channel 934, and a third sub-channel 936 that are sequentially communicated. The first sub-channel 932 is formed by enclosing a sidewall of the atomizing portion 928, a sidewall of the liquid guiding portion 929, and an inner wall of the atomizing chamber 820. The second sub-channel 934 is located inside the liquid guiding portion 929, and the second sub-channel 934 extends from the side surface 925 towards the interior of the liquid guiding portion 929 and further extends through the liquid guiding portion 929. The third sub-channel 936 is formed by enclosing a side wall of the liquid absorbing portion 926, a side wall of the other side of the liquid guiding portion 929, and the inner wall of the atomizing chamber 820, and the third sub-channel 936 is in communication with the inhalation channel 860. The airflow enters the atomizing chamber 820 from the air inlet 882. The atomizing surface 924 generates an atomizing effect. The airflow takes away the smoke at the atomizing surface 924, enters the first sub-channel 932, then enters the third sub-channel 936 through the second sub-channel 934, and finally enters the user's mouth through the inhalation channel 860 and the air outlet 884.

The liquid absorbing surface 922 is used for absorbing the liquid from the liquid storage chamber 840. The heat generating structure 940 on the atomizing surface 924 is used for atomizing the liquid. The smoke generated at the atomizing surface 924 enters the airflow channel along together with the airflow. At least one segment of the airflow channel extends from the side surface towards the interior of the porous body 920. The airflow can take away the heat in the porous body 920, avoiding an internal overheat of the porous body 920 from resulting in an expansion of the liquid or gas in the porous body 920, and avoiding a high fluid pressure in the porous body 920 from impeding a transmission of the liquid, therefore improving a liquid guiding effect of the porous body 920. At the same time, as the airflow can generate a negative pressure, the negative pressure can further accelerate the transport of the liquid.

Although the respective embodiments have been described one by one, it shall be appreciated that the respective embodiments will not be isolated. Those skilled in the art can apparently appreciate upon reading the disclosure of this application that the respective technical features involved in the respective embodiments can be combined arbitrarily between the respective embodiments as long as they have no collision with each other.

The above-mentioned embodiments merely present several embodiments of the present disclosure, which are described specifically and in detail but should not be interpreted as limit to the scope of the present disclosure. It should be noted that those skilled in the art may make various modifications and improvements without departing from the concept of the present disclosure, all of which fall in the protection scope of the present disclosure. Therefore, the protection scope of the present disclosure shall be subject to the appended claims.

What is claimed is:

1. An electronic atomizing device, comprising:
a body defining a liquid storage chamber and an inhalation channel; and
an atomizing element comprising a porous body and a heat generating structure, the porous body comprising a liquid absorbing surface, an atomizing surface, and a side surface connecting the liquid absorbing surface and the atomizing surface, the liquid absorbing surface being configured to absorb liquid from the liquid storage chamber, the heat generating structure being located on the atomizing surface, the porous body forming an airflow channel that is in communication with the inhalation channel, and at least one segment of the airflow channel extending from the side surface towards an interior of the porous body;

wherein the at least one segment of the airflow channel is located between the atomizing surface and the liquid absorbing surface.

2. The electronic atomizing device according to claim 1, wherein the porous body comprises a liquid absorbing portion, an atomizing portion, and a liquid guiding portion located therebetween, which are integrally formed; the liquid absorbing surface is located at a side of the liquid absorbing portion away from the liquid guiding portion, and the atomizing surface is located at a side of the atomizing portion away from the liquid guiding portion.

3. The electronic atomizing device according to claim 2, wherein the airflow channel comprises a plurality of sub-channels, the sub-channels comprise a first, a second, and a third sub-channel that are sequentially communicated, the first sub-channel is formed by enclosing a sidewall of the atomizing portion, a sidewall of the liquid guiding portion, and an inner wall of the body, the second sub-channel is located inside the liquid guiding portion and located between the atomizing surface and the liquid absorbing surface, the second sub-channel extends from the side surface towards the interior of the liquid guiding portion and further extends through the liquid guiding portion, the third sub-channel is located inside the liquid absorbing portion, and the third sub-channel is in communication with the inhalation channel.

4. The electronic atomizing device according to claim 3, wherein the electronic atomizing device comprises two of the first sub-channels and two of the second sub-channels, the number of the third sub-channel is one, the third sub-channel is located in a middle portion of the liquid absorbing portion, one end of each of the two second sub-channels is in communication with each of the two first sub-channels, respectively, the other end of each of the two second sub-channels are both in communication with the third sub-channel.

5. The electronic atomizing device according to claim 3, wherein the body comprises a liquid reservoir, the liquid reservoir comprises an inner tube and an outer tube;
the inhalation channel is located inside the inner tube, an end of the inner tube extends into the third sub-channel, so that the inhalation channel is in communication with the third sub-channel, the other end of the inner tube forms a absorbing port;
the inner tube is received in the outer tube, the liquid storage chamber is located between the outer tube and the inner tube, and the liquid storage chamber has an opening facing the atomizing element; and
the atomizing element is located in the outer tube and is adjacent to the liquid storage chamber, the liquid absorbing surface faces the liquid storage chamber and covers the opening of the liquid storage chamber.

6. The electronic atomizing device according to claim 5, wherein the body further comprises a flow restricting member, the flow restricting member defines a mounting hole matching the internal tube, the flow restricting member is sleeved on the inner tube via the mounting hole, the flow restricting member is located at a junction position between the liquid storage chamber and the liquid absorbing surface, at least one of an outer wall of the inner tube and an inner wall of the outer tube is provided with a stepped portion, and the flow restricting member is latched on the stepped portion.

7. The electronic atomizing device of claim 5, wherein the body further comprises a connecting structure, the atomizing element is fixed in the outer tube by the connecting structure, the connecting structure further comprises a confining tube and a blocking member, the confining tube is sleeved on an outer wall of the outer tube, the electrical connecting assembly abuts against an inner wall of the outer tube, a position of the confining tube corresponds to a position of the electrical connecting assembly, the blocking member extends into the confining tube, and an end of the blocking member abuts against the outer tube and the electrical connecting assembly.

8. The electronic atomizing device according to claim 3, wherein the atomizing element further comprises a sealing gasket, the sealing gasket enwraps the porous body, the sealing gasket covers the liquid absorbing surface and a junction portion between the liquid absorbing portion and the inner tube, and the sealing gasket covering the liquid absorbing surface defines a flow restricting hole.

9. The electronic atomizing device according to claim 8, wherein the sealing gasket further covers the sidewalls of the atomizing portion and the liquid guiding portion, which are configured to form the first sub-channel.

10. The electronic atomizing device according to claim 2, wherein the airflow channel comprises a plurality of sub-channels, the sub-channels comprise a first sub-channel, a second sub-channel, and a third sub-channel that are sequentially communicated, the first sub-channel is formed by enclosing a sidewall of the atomizing portion, a first sidewall of the liquid guiding portion, and an inner wall of the body, the second sub-channel is located inside the liquid guiding portion and located between the atomizing surface and the liquid absorbing surface, the second sub-channel extends from the side surface towards the interior of the liquid guiding portion, and further extends through the liquid guiding portion, the third sub-channel is formed by enclosing a sidewall of the liquid absorbing portion, a second sidewall of the liquid guiding portion opposite to the first sidewall, and the inner wall of the body, and the third sub-channel is in communication with the inhalation channel.

11. The electronic atomizing device according to claim 1, wherein the body further comprises a connecting structure, the atomizing element is fixed in the body by the connecting structure, and the connecting structure defines an air inlet aligned with the atomizing surface.

12. The electronic atomizing device according to claim 11, wherein an axial direction of the air inlet is perpendicular to the atomizing surface.

13. The electronic atomizing device according to claim 12, wherein the connecting structure comprises an electrical connecting assembly and a wire positioning member, the wire positioning member is disposed on the electrical connecting assembly, and the wire positioning member defines a wire hole configured to limit a position of a wire of the heat generating structure.

14. The electronic atomizing device according to claim 1, wherein the heat generating structure is a heating film or a heating circuit layer.

15. The electronic atomizing device according to claim 14, wherein the heating film is a porous heating film, the porous heating film is formed on the atomizing surface by a vapor deposition method, and a thickness of the porous heating film is in a range from 0.5 μm to 1.5 μm.

16. The electronic atomizing device according to claim 15, wherein an aperture of a micropore on the porous heating film is in a range from 5 μm to 30 μm.

17. The electronic atomizing device according to claim 15, wherein the thickness of the porous heating film is less than an aperture of a micropore on the porous body.

18. The electronic atomizing device according to claim 1, further comprising a wire configured to supply power to the heat generating structure, wherein one end of the wire extends from the atomizing surface through the porous body and is welded and fixed on the liquid absorbing surface.

19. The electronic atomizing device according to claim 1, wherein the porous body is a porous ceramic body, an aperture of a micropore on the porous body is in a range from 1 μm to 100 μm, and a porosity of the porous body is in a range from 30% to 83%.

* * * * *